United States Patent [19]

Toole et al.

[11] Patent Number: 5,840,867
[45] Date of Patent: Nov. 24, 1998

[54] APTAMER ANALOGS SPECIFIC FOR BIOMOLECULES

[75] Inventors: John J. Toole, Burlingame; Linda C. Griffin, Atherton; Louis C. Bock, Foster City; John A. Latham, Palo Alto, all of Calif.

[73] Assignee: Gilead Sciences, Inc., Foster City, Calif.

[21] Appl. No.: 237,973

[22] Filed: May 3, 1994

Related U.S. Application Data

[63] Continuation-in-part of Ser. No. 658,849, Feb. 21, 1991, abandoned, and a continuation of Ser. No. 787,921, Nov. 6, 1991, abandoned, which is a continuation-in-part of Ser. No. 745,215, Aug. 14, 1991, abandoned, which is a continuation-in-part of Ser. No. 659,981, Feb. 21, 1991, abandoned.

[51] Int. Cl.$^6$ .......................... C07H 21/04; C07H 21/02; C12Q 1/68
[52] U.S. Cl. .............................. 536/23.1; 435/6; 935/77; 935/78
[58] Field of Search ................................ 435/6; 536/23.1

[56] References Cited

U.S. PATENT DOCUMENTS

| | | | |
|---|---|---|---|
| 4,647,529 | 3/1987 | Rodland et al. | 435/6 |
| 4,748,156 | 5/1988 | Aoki et al. | 514/21 |
| 5,133,866 | 7/1992 | Kauvar | 210/635 |
| 5,270,163 | 12/1993 | Gold et al. | |

FOREIGN PATENT DOCUMENTS

| | | |
|---|---|---|
| WO/91/19813 | 12/1991 | WIPO . |
| 92/05285 | 4/1992 | WIPO . |

OTHER PUBLICATIONS

Fenton II et al., "Thrombin Anion–binding Exosite Interactions with Heparin and Various Polyanions," *Annals New York Academy of Sciences* Jul. 8, 1991 pp. 158–165.

Oliphant et al., "Defining the consensus sequences of *E. coli* promoter elements by random selection," *Nucl. Acids Res.* 16(5):7673–7683 (1988).

Oliphant et al., "Defining the Sequence Specificity of DNA–Binding Proteins by Selecting Binding Sites from Random–Sequence Oligonucleotides: Analysis of Yeast GCN4 Protein," *Mol. and Cell. Biol.* 9(7):2944–2949 (1989).

Chittenden et al., "The T/E1A–Binding Domain of the Retinoblastoma Product Can Interact Selectively with a Sequence–Specific DNA–Binding Protein," *Cell* 65:1073–1082 (Jun. 14, 1991).

Abelson, "Directed Evolution of Nucleic Acids by Independent Replication and Selection," *Science* (1990) 240:488–489.

Ötvös et al., "Substrate specificity of DNA polymerases. I. Enzyme–catalysed incorporation of 5–(1–alkenyl)–2'–deoxyuridines into DNA," *Nucl. Acid Res* (1987) pp. 1763–1777.

Allen et al., "Fluoresence Oligonucleotides and Deoxynucleotide Triphosphates: Preparation and Their Interaction with the Large (Klenow) Fragment of *Escherichia coli* DNA Polymerase I," *Biochemistry* (1989) 28:4601–4607.

Langer et al., "Enzymatic synthesis of biotin–labeled polynucleotides: Novel nucleic acid affinity probes," *Proc. Natl. Acad. Sci. USA* (1981) 78:6633–6637.

Gebeyehu et al., "Novel biotinylated nucleotide — analogs for labelling and colorimetric detection of DNA," *Nucleic Acids Res* (1987) 15:4513.

Gillam et al., "N$^4$(6–Aminohexyl)cytidine and –deoxycytidine Nucleotides Can Be Used to Label DNA," *Anal. Biochem.* (1986) 199–207.

Trainor et al., "A procedure for the preparation of fluorescence–labeled DNA with terminal deoxynucleotidyl transferase," *Nucl. Acid Res.* (1988) 16:11846.

Mizusawa et al., "Improvements of the dideoxy chain termination method of DNA sequencing by use of deoxy–7–deazaguanosine triphosphate in place of dGTP," *Nucl. Acid Res.* (1986) 14:1319–1324.

Evans et al., "Synthesis and Biological Properties of 5–Azido–2'–deoxyuridine 5'–Triphosphate, a Photoactive Nucleotide Suitable for Making Light–Sensitive DNA," *Biochemistry* (1987) 26:269–276.

Evans et al., "5–Azido–2'–deoxyuridine 5'–triphosphate: A photoaffinity–leveling reagent and tool for the enzymatic synthesis of photoactive DNA," *Proc. Natl. Acad. Sci. USA* (1986) 83:5832–5386.

Dale et al., "The Synthesis and Enzymatic Polymerization of Nucleotides Containing Mercury: Potential Tools for Nucleic Acid Sequencing and Structural Analysis," *Proc. Natl. Acad. Sci. USA* (1973) 70:2238–2242.

Prober et al., "A System for Rapid DNA Sequencing with Fluoresence Chain–Terminating Dideoxynucleotides," *Science* 238:336–341.

Valkó et al., "Correlation of Nucleotide Incorporation Rate and PHLA Retention Parameters of Substituted Nucleosides," *J. Liq. Chromatography* (1989) 12(11):2103–2116.

Valkó et al., "Application of chromatographic retention data in an investigation of quantitative structure — nucleotide incorporation rate relationship," *J. Chromatography* (1990) 506:35–44.

Huynh–Dinh et al. *Proc. Natl. Acad. Sci.* (1985) 82:7510–7514.

(List continued on next page.)

*Primary Examiner*—Stephanie W. Zitomer
*Attorney, Agent, or Firm*—Mark L. Bosse

[57] ABSTRACT

Oligonucleotide sequences that mediate specific binding to selected target molecules and contain modified base, sugars, or sugar linkages are disclosed. Single-stranded DNA oligomers are obtained that bind to a series of biomolecules that differ in both size and composition. The range of target molecules that may be bound permits generation of binding oligomers that are specific for binding to nearly any biomolecule that is composed of amino acids, lipids and/or carbohydrates. The binding oligomers are useful for therapeutic, diagnostic and manufacturing purposes.

4 Claims, 1 Drawing Sheet

OTHER PUBLICATIONS

Nishikawa A., "Chromatograhy, Affinity," *Kirk–Othmer, Encyclopedia of Chemical Technology* (1979) John Wiley & Sons, New York, Third Edition, 6:35–54.

Blackwell et al., *Science* (1990) 250:1104–1110.

Blackwell et al., *Science* (1990) 250:1149–1152.

Tuerk and Gold, *Science* (1990) 249:505–510.

Joyce, G.F., *Gene* (1989) 82:83–87.

Kinzler and Vogelstein, *Nucleic Acids Res.* (1989) 17:3645–3653.

Kinzler and Vogelstein, *Mol. Cell Biol.* (1990) 10:634–642.

Ellington and Szostak, *Nature* (1990) 346:818–822.

Thiesen and Bach, *Nucleic Acids Res.* (1990) 18(11):3203–3208.

Oliphant et al., "The Use of Random–Sequence Oligonucleotides for Determining Consensus Sequences," *Methods in Enzymology,* 155:568–582 (1987).

Andrake et al., "DNA polymerase of bacteriophage T4 is an autogenous translational repressor," *PNAS,* 85:7942–7946 (Nov. 1988).

Hanson et al., "Interruption of acute platelet–dependent thrombosis by the synthetic antithrombin–D–pheylalanyl––L–arginyl chloromethyl ketonen," *PNAS, USA,* 85:3184–3188 (May 1988).

Prescott et al., "Human endothelial cells in culture produce platelet–activating factor (1–alkyl–2–acetyl–sn–glycero–3–phosphocholine) when stimulated with thrombin," *PNAS, USA* 81:3534–3538, (Jun. 1984).

Shaw et al., "Modified deoxyoligonucleotides stable to exonuclease degradation in serum," *Nucl. Acids Res.,* 19(4):747–750 (1991).

Riordan et al., "Oligonucleotide–based therapeutics," *Nature,* 350:442–3 (Apr. 4, 1991).

Kirk–Othmer, "Encyclopedia of Chemical Technology," 3rd Ed. 6 (1979) J. Wiley & Sons (N.Y.) pp. 35–54.

Lestienng et al.., Biochimie 65:49–52 (1983).

Zon, Pharm. Res. 5(9):539–549.

Lehninger, *Biochemistry,* $2^{th}$ ed., Worth Publishers, Inc., 1975. 1104 pp. 1013–1014.

| #  | *  |   |   |   |   |   |   |   |   |   |   |   |   |   |   |   | * |   |
|----|----|---|---|---|---|---|---|---|---|---|---|---|---|---|---|---|---|---|
| 1  | 26 | G | G | G | T | T | G | G | - | - | G | T | C | G | G | T | T | G | G | T |
| 2  | 20 | G | G | G | A | T | G | G | - | - | T | T | T | G | G | T | T | G | G | G |
| 3  | 32 | A | G | G | T | T | G | G | - | - | - | G | A | G | G | T | G | G | G |
| 4  | 41 | T | G | G | T | T | G | G | - | - | C | G | A | G | G | A | T | G | G | A |
| 5  | 56 | A | G | G | T | T | G | G | - | G | T | A | G | T | G | T | T | G | G | T |
| 6  | 29 | A | G | G | T | T | G | G | - | - | G | C | T | G | G | T | T | G | G | G |
| 7  | 17 | G | G | G | T | T | G | G | - | - | - | G | A | G | G | T | T | G | G | A |
| 8  | 44 | T | G | G | T | T | G | G | - | - | G | T | C | G | G | T | T | G | G | G |
| 9  | 50 | G | G | G | A | T | G | G | - | - | T | G | T | G | G | T | T | G | G | C |
| 10 | 30 | T | G | G | T | T | G | G | - | - | C | A | G | G | A | T | G | G | G |
| 11 | 25 | T | G | G | A | T | G | G | - | - | T | G | A | G | G | T | T | G | G | A |
| 12 | 28 | G | G | G | T | G | G | - | - | T | T | A | G | G | T | T | G | G | T |
| 13 | 47 | A | G | G | T | G | G | - | - | T | T | A | G | G | T | T | G | G | T |
| 14 | 42 | C | G | G | T | T | G | G | - | G | T | T | G | G | A | T | G | G | A |
| 15 | 41 | C | G | G | T | T | G | G | - | - | T | G | T | G | G | T | T | G | G | T |
| 16 | 53 | A | G | G | T | T | G | G | - | - | T | G | T | G | G | T | G | G | G |
| 17 | 15 | C | G | G | T | G | G | - | - | A | T | A | G | G | T | T | G | G | A |
| 18 | 24 | G | G | T | G | T | G | G | T | A | G | T | T | T | G | T | T | G | G | G |
| 19 | 23 | T | G | G | T | T | G | G | T | T | A | C | T | G | G | T | T | G | G | G |
| 20 | 27 | G | G | G | T | T | G | G | - | - | T | C | T | G | G | T | G | G | A |
| 21 | 36 | T | G | G | T | T | G | G | - | - | G | T | T | G | G | G | T | G | G | A |
| 22 | 25 | T | G | G | T | T | G | G | - | - | C | C | A | G | G | T | T | G | G | A |
| 23 | 12 | C | T | A | G | C | G | G | - | C | A | G | T | G | G | T | T | G | G | G |
| 24 | 25 | T | G | G | G | T | G | G | - | - | G | G | A | G | G | T | T | G | G | T |
| 25 | 49 | A | G | G | T | T | G | G | - | - | T | T | T | G | G | G | T | G | G | T |
| 26 | 28 | A | G | G | T | T | G | G | - | T | T | A | G | G | T | T | G | G | T |
| 27 | 18 | G | G | G | A | T | G | C | - | - | G | G | T | G | G | T | T | G | G | G |
| 28 | 55 | T | G | G | T | T | G | G | - | T | T | A | T | G | G | T | T | G | G | T |
| 29 | 23 | A | G | G | T | T | G | G | - | - | T | G | T | G | G | T | T | G | G | C |
| 30 | 40 | A | G | G | T | T | G | G | - | - | T | G | T | G | G | G | T | G | G | G |
| 31 | 41 | T | G | G | T | T | G | G | - | - | - | G | A | G | G | T | T | G | G | T |
| 32 | 42 | G | G | G | T | T | G | G | T | G | G | T | G | G | A | T | G | G | T |
|    |    |   |   |   |   | Consensus Sequence |   |   |   |   |   |   |   |   |   |   |   |   |   |
|    |    |   | G | G | T | T | G | G |   | (N)3 |   |   |   | G | G | T | T | G | G |   |
| G  |    |   | 9 | 31| 30| 6 | 0 | 32| 31|   |   |   |   |   | 30| 32| 6 | 0 | 32| 32| 11 |
| A  |    |   | 9 | 0 | 1 | 4 | 0 | 0 | 0 |   |   |   |   |   | 0 | 0 | 4 | 0 | 0 | 0 | 8 |
| T  |    |   | 10| 1 | 1 | 22| 31| 0 | 0 |   |   |   |   |   | 2 | 0 | 22| 32| 0 | 0 | 11 |
| C  |    |   | 4 | 0 | 0 | 0 | 1 | 0 | 1 |   |   |   |   |   | 0 | 0 | 0 | 0 | 0 | 0 | 2 |

Fig. 1

APTAMER ANALOGS SPECIFIC FOR BIOMOLECULES

CROSS-REFERENCE TO RELATED APPLICATIONS

This is a continuation of application Ser. No. 07/787,921 filed on Nov. 6, 1991, now abandoned, which is a continuation-in-part of U.S. application Ser. No. 745,215, filed Aug. 14, 1991, now abandoned, which is itself a continuation-in-part of copending U.S. application Ser. No. 659,981, filed Feb. 21, 1991, now abandoned, the disclosures of which are hereby incorporated by reference in their entirety. This application is also a continuation-in-part of U.S. application Ser. No. 09/658,849, filed Feb. 21, 1991, now abandoned. This application is also related to the following copending U.S. applications filed on Feb. 21, 1991, each of which is hereby incorporated by reference in its entirety: (1) Method for Generating Aptamers of Non-Predetermined or Substantially Non-Predetermined Sequences, U.S. Ser. No. 659,980, now abandoned; (2) Aptamers Specific for Eicosanoids, U.S. Ser. No. 659,103, now abandoned; (3) Aptamers for Cell Surface Ligands, U.S. Ser. No. 658,796, now abandoned; (4) Use of Novel Oligonucleotides in Target Specific Binding, U.S. Ser. No. 658,849, now abandoned; (5) Immune Recruitment, U.S. Ser. No. 659,113, now abandoned; and (6) Aptamers Specific for Kinins, U.S. Ser. No. 659,114, now abandoned.

TECHNICAL FIELD

This invention is in the field of rational drug design using biomolecule targeting and aptamer development. The invention discloses and claims methods for making aptamers to biomolecular targets such as proteins in general, and thrombin in particular, and the aptamers resulting therefrom. The novel compounds and methods herein disclosed and claimed may be applied broadly to biotechnology diagnostics and therapeutics. More specifically, this invention is related to aptamers that bind to a specific biomolecule and interfere with its normal biological function, wherein the aptamers contain one or more modified sugars, bases, or linkages between the backbone sugar residues.

BACKGROUND AND RELATED ART

Conventional methods of detection and isolation of proteins and other molecules have employed antibodies and the like which specifically bind such substances. Recently, however, the de novo design of specifically binding oligonucleotides for non-oligonucleotide targets that generally bind nucleic acids has been described. See, e.g., Blackwell, T. K., et al., *Science* (1990) 250:1104–1110; Blackwell, T. K., et al., *Science* (1990) 250:1149–1152; Tuerk, C., and Gold, L., *Science* (1990) 249:505–510; Joyce, G. F., *Gene* (1989) 82:83–87. Such oligonucleotides have been termed "aptamers" herein. Tuerk and Gold describe the use of a procedure termed "systematic evolution of ligands by exponential enrichment." In this method, a pool of RNAs that are completely randomized at specific positions is subjected to selection for binding by a desired nucleic acid-binding protein which has been fixed on a nitrocellulose filter. The bound RNAs then are recovered and amplified as double-stranded DNA that is competent for subsequent in vitro transcription. The newly transcribed RNA then is recycled through this procedure to enrich for oligonucleotides that have consensus sequences for binding by the cognate protein. The oligonucleotides so obtained then may be sequenced for further study. Tuerk and Gold applied this procedure to identify RNA oligonucleotides which are bound by the RNA binding region of T4 DNA polymerase.

Kinzler, K. W., et al., *Nucleic Acids Res.* (1989) 17:3645–3653, applied this technique to identify double-stranded DNA sequences that were bound by proteins that bind to DNA and regulate gene expression. In the reported work, total genomic DNA is first converted to a form that is suitable for amplification by PCR by ligation of linker sequences to the genomic DNA fragments and the DNA sequences of interest are selected by binding mediated by the target regulatory protein. The recovered bound sequences are then amplified by PCR. The process of binding by protein and amplification are repeated as needed. The selection and amplification process are repeated as needed. The process as described was applied to identify DNA sequences which bind to the *Xenopus laevis* transcription factor 3A. The same authors (Kinzler et al.) in a later paper, *Mol. Cell Biol.* (1990) 10:634–642, applied this same technique to identify the portion of the human genome which is bound by the GLI gene product produced as a recombinant fusion protein. The GLI gene is amplified in a subset of human tumors.

Ellington, A. D., et al., *Nature* (1990) 346: 818–822, describe the production of a large number of random sequence RNA molecules and identification of those which bind specifically to immobilized target molecules, in the case of this paper, to specific dyes such as Cibacron blue. Randomly synthesized DNA yielding approximately $10^{15}$ individual sequences was amplified by PCR and transcribed into RNA. It was thought that the complexity of the pool was reduced in the amplification/transcription steps to approximately $10^{13}$ different sequences. The pool was then applied to an affinity column containing the dye and the bound sequences subsequently eluted, treated with reverse transcriptase and amplified by PCR. The results showed that about one in $10^{10}$ random sequence RNA molecules folds in such a way as to bind specifically to the ligand.

Thiesen, H.-J., and Bach, C., *Nucleic Acids Res.* (1990) 18:3203–3208, describe what they call a target detection assay (TDA) to determine double-stranded DNA binding sites for putative DNA binding proteins. In their approach, a purified functionally active DNA binding protein and a pool of random double-stranded oligonucleotides which contain PCR primer sites at each end were incubated with the protein. The resulting DNA complexes with the protein (in their case, the SP-1 regulatory protein) were separated from the unbound oligomers in the random mixture by band-shift electrophoresis and the SP-1 bound oligonucleotides were rescued by PCR and cloned, and then sequenced.

Copending U.S. application Ser. No. 07/586,769, filed Sep. 21, 1990, the entire disclosure of which is hereby-incorporated by reference, describes a method utilizing a binding site selection technique which depends on the availability of PCR (polymerase chain reaction). In this approach, selected and amplified oligonucleotides were used to identify consensus DNA recognition sequences used by DNA binding proteins under study.

None of the cited references describe the use of single-stranded DNA as an appropriate material for generating aptamers. The use of DNA aptamers has several advantages over RNA including increased nuclease stability, in particular plasma nuclease stability, and ease of amplification by PCR or other methods. RNA generally is converted to DNA prior to amplification using reverse transcriptase, a process that is not equally efficient with all sequences, resulting in loss of some aptamers from a selected pool.

Finally, none of the above references describes (i) the identification of oligonucleotides which specifically bind biomolecules such as thrombin which do not normally bind to DNA or RNA; (ii) interference with their normal biological function as a result of binding; or (iii) use of linkages other than the standard phosphodiester linkages in the backbone of the oligonucleotide.

SUMMARY OF THE INVENTION

The identification of oligonucleotides that specifically bind to biomolecules that do not normally bind to RNA or DNA has now been demonstrated for a number of biomolecules that vary widely in size, structure and composition. These molecules include: (1) thrombin, a multifunctional regulatory protein that converts fibrinogen to fibrin in the process of clot formation; (2) bradykinin, a nonapeptide kinin involved in blood pressure regulation and implicated in hypotension; (3) PGF2α, a prostaglandin or fatty acid derivative that exhibits hormonal activity. Additionally, the interaction of oligonucleotides with biomolecules whose natural biological function is primarily extracellular has now been demonstrated.

This invention is directed to a method for making aptamers to biomolecules, including proteins, polypeptides and hormones, more specifically to thrombin, bradykinin and PGF2α. The invention is also directed to aptamer compositions that bind to biomolecules, thereby interfering with their normal biological function.

In one aspect, the invention is directed to a method to determine an aptamer which binds specifically to a biomolecular target such as thrombin, which method comprises providing a mixture containing oligomers having portions which form a random set of sequences and, optionally, portions which permit amplification of the oligomers, incubating the oligomer mixture with the target substance coupled to a support to form complexes between the target and the oligomers bound specifically thereto, removing the unbound members of the oligo-nucleotide mixture from the support environment, recovering the complexed oligonucleotides by uncoupling the target substance from the support, amplifying the recovered oligonucleotides, and sequencing the recovered and amplified oligonucleotides which had been complexed with the target. In a preferred embodiment, the mixture of oligonucleotides having random sequences also contains a sequence or sequences that permit binding to the target. In a particularly preferred embodiment, the oligonucleotide mixture is single-stranded DNA.

In other aspects, the invention is directed to oligonucleotides which contain sequences identified by the above method, and to oligonucleotide sequences which bind specifically to thrombin. In still another aspect, the invention is directed to complexes comprising the thrombin target substance and specifically bound oligomer.

In still other aspects, the invention is directed to oligomers which contain sequences that bind specifically to thrombin target substances and inhibit its normal biological function, and to the use of these oligomers in therapy, diagnostics, and purification procedures.

In yet another aspect, this invention is directed to single-stranded deoxyribonucleotides that bind specifically to biomolecules. It has been heretofore thought that the three-dimensional structure of double-stranded DNA limited the structural diversity of the molecule. The inventors herein are unaware of any prior demonstration of structural diversity for single-or double-stranded DNA sufficient to provide the range of conformations necessary to provide aptamers to biomolecules.

In yet a further aspect, this invention is directed to oligomers which contain sequences that bind specifically to target substances and inhibit their normal biological function, and which also contain one or more modified bases, sugars, or sugar linkages, and to the use of these oligomers in therapy, diagnostics, and purification procedures.

These and other embodiments also may be used to generate aptamers to other biomolecules such as proteins, polypeptides, short peptides, enzymes, lipids, glyco-lipids, phospholipids, leukotrienes, glycoproteins, carbohydrates, or cell surface molecules such as receptors, ion channels or extracellular matrix molecules, that bind to the biomolecules and affect their normal biological function.

BRIEF DESCRIPTION OF THE FIGURE

FIG. 1 is a chart depicting thrombin aptamer consensus-related sequences (SEQ ID NO:31)(SEQ ID NO:32)(SEQ ID NO:33)(SEQ ID NO:34)(SEQ ID NO:35)(SEQ ID NO:36)(SEQ ID NO:37)(SEQ ID NO:38)(SEQ ID NO:39) (SEQ ID NO:40)(SEQ ID NO:41)(SEQ ID NO:42)(SEQ ID NO:43)(SEQ ID NO:44)(SEQ ID NO:45)(SEQ ID NO:46) (SEQ ID NO:47)(SEQ ID NO:48)(SEQ ID NO:49)(SEQ ID NO:50)(SEQ ID NO:51)(SEQ ID NO:52)(SEQ ID NO:53) (SEQ ID NO:54)(SEQ ID NO:55)(SEQ ID NO:56)(SEQ ID NO:57)(SEQ ID NO:58)(SEQ ID NO:59)(SEQ ID NO:60) (SEQ ID NO:61)(SEQ ID NO:62).

MODES OF CARRYING OUT THE INVENTION

The practice of the present invention encompasses conventional techniques of chemistry, molecular biology, biochemistry, protein chemistry, and recombinant DNA technology, which are within the skill of the art. Such techniques are explained fully in the literature. See, e.g., *Oligonucleotide Synthesis* (M. J. Gait ed. 1984); *Nucleic Acid Hybridization* (B. D. Hames & S. J. Higgins, eds., 1984); Sambrook, Fritsch & Maniatis, *Molecular Cloning: A Laboratory Manual*, Second Edition (1989); *PCR Technology* (H. A. Erlich ed., Stockton Press); R. K. Scope, *Protein Purification Principles and Practice* (Springer-Verlag); and the series *Methods in Enzymology* (S. Colowick and N. Kaplan eds., Academic Press, Inc.).

All patents, patent applications and publications mentioned herein, whether supra or infra, are hereby incorporated by reference in their entirety.

The invention is directed to a method which permits the recovery and deduction or identification of aptamers which bind specifically to desired targets, including polypeptides, short peptides, enzymes, proteins, lipids, glycolipids, phospholipids, leukotrienes, glycoproteins, carbohydrates, or cell surface molecules such as receptors, ion channels or extracellular matrix molecules. More specifically desired targets include thrombin, bradykinin, and PGF2α. As a result of application of this method, aptamers which contain the specifically binding sequences can be prepared and used in oligonucleotide-based therapy, in the detection and isolation of the target substance, as well as in other applications.

For example, these aptamers can be used as a separation tool for retrieving the targets to which they specifically bind. In these methods, the aptamers function much like monoclonal antibodies in their specificity and usage. By coupling the aptamers containing the specifically binding sequences to a solid support, desired target substances can be recovered in useful quantities. In addition, these aptamers can be used in diagnosis by employing them in specific binding assays for the target substances. When suitably labeled using detectable moieties such as radioisotopes, the specifically binding oligonucleotides can also be used for in vivo imaging or histological analysis.

Furthermore, when the aptamer specifically binds to biologically active sites on a biomolecule, that aptamer can be used therapeutically to affect that biological activity.

"Oligomers" or "oligonucleotides" include RNA or DNA sequences of more than one nucleotide in either single chain or duplex form and specifically includes short sequences such as dimers and trimers, in either single chain or duplex form, which may be intermediates in the production of the specifically binding oligonucleotides. "Nucleic acids", as used herein, refers to RNA or DNA sequences of any length in single-stranded or duplex form.

As used herein, the term "aptamer" or "specifically binding oligonucleotide" refers to an oligonucleotide that is capable of forming a complex with an intended target substance. The complexation is target-specific in the sense that other materials which may accompany the target do not complex to the aptamer. It is recognized that complexation and affinity are a matter of degree; however, in this context, "target-specific" means that the aptamer binds to target with a much higher degree of affinity than it binds to contaminating materials. The meaning of specificity in this context is thus similar to the meaning of specificity as applied to antibodies, for example.

The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

The aptamers of the present invention are capable of binding target molecules which are not known to bind nucleic acids as their biological function. By "biological function" is meant any activity that the target possesses in the normal context of its metabolic or other in vivo function in the organism. By way of example and without limiting the present invention, a biological function may be the catalytic function of an enzyme, the regulatory function of a hormone, or the recognition function of an immunomolecule or cell surface molecule. Thus, as used herein, "biological function" refers to those activities that take place in the intact organism. It does not include activities which might be demonstrated in a completely artificial context in vitro and which are not duplicated in the "natural" context of the organism; nor does it include the generalized toxic effects resulting from the presence of a molecule in excess of its naturally-occurring concentration.

In "affecting" biological function of a target, the aptamers of the invention will alter the "biological function" of the target as that term is defined above. Of course, the effect on the biological function may be demonstrated in counterpart in vitro tests which are indicative of the corresponding biological function in vivo. The "effect" is usually an inhibition; however, in some instances an agonistic effect may also be found. For example, aptamers which specifically bind receptors may behave either as antagonists or agonists for the ligand that ordinarily binds such receptors.

The target molecules that the aptamers of the invention specifically bind do not ordinarily bind nucleic acids as part of their biological function in the sense defined above. Of course, the aptamers do in fact bind the target; however, the role of the target in metabolism does not include the binding of RNA or DNA in situ. In certain instances, though, a target molecule may have more than one biological function, wherein one such function is the binding of nucleic acids. Aptamers that bind to such target molecules to effect the non-nucleic-acid-binding biological function in a way not possible by normal nucleic acid binding to the target are also within the scope of this invention.

As used herein, the term "binding" refers to an interaction or complexation between a target and an oligonucleotide or aptamer, resulting in a sufficiently stable complex so as to permit separation of oligonucleotide:target complexes from uncomplexed oligonucleotides under given binding complexation or reaction conditions. Binding is mediated through hydrogen bonding or other molecular forces. As used herein, the term "binding" specifically excludes the normal "Watson-Crick"-type binding interactions (i.e., adenine-thymine and guanine-cytosine base-pairing) traditionally associated with the DNA double helix.

In general, a minimum of approximately 3 nucleotides, preferably at least 5 nucleotides, are necessary to effect specific binding. The only apparent limitations on the binding specificity of the target/oligonucleotide complexes of the invention concern sufficient sequence to be distinctive in the binding oligonucleotide and sufficient binding capacity of the target substance to obtain the necessary interaction. Oligonucleotides of sequences shorter than 10 may also be feasible if the appropriate interaction can be obtained in the context of the environment in which the target is placed. Although the oligonucleotides generally described herein are single-stranded or double-stranded, it is contemplated that aptamers may sometimes assume triple-stranded or quadruple-stranded structures.

As further explained below, the specifically binding oligonucleotides need to contain the sequence-conferring specificity, but may be extended with flanking regions and otherwise derivatized or modified.

The aptamers found to bind to the targets may be isolated, sequenced, and then resynthesized as conventional DNA or RNA moieties, or may be "modified" oligomers which are those conventionally recognized in the art. These modifications include, but are not limited to incorporation of: (1) modified or analogous forms of sugars (ribose and deoxyribose); (2) alternative linking groups; or (3) analogous forms of purine and pyrimidine bases.

As the resulting aptamers of the invention include intermediates in their synthesis, any of the hydroxyl groups ordinarily present may be replaced by phosphonate groups, phosphate groups, protected by a standard protecting group, or activated to prepare additional linkages to additional nucleotides, or may be conjugated to solid supports. The 5' terminal OH is conventionally free but may be phosphorylated; OH substituents at the 3' terminus may also be phosphorylated. The hydroxyls may also be derivatized to standard protecting groups.

One or more phosphodiester linkages may be replaced by alternative linking groups. These alternative linking groups include, but are not limited to embodiments wherein P(O)O is replaced by P(O)S ("thioate"), P(S)S ("dithioate"), P(O)NR$_2$ ("amidate"), P(O)R, P(O)OR', CO or CH$_2$ ("formacetal"), wherein each R or R' is independently H or substituted or unsubstituted alkyl (1–20C.) optionally containing an ether (—O—) linkage, aryl, alkenyl, cycloalkyl, cycloalkenyl or aralkyl. A preferred set of R substitutions for the P(O)NR$_2$ group are hydrogen and methoxyethyl. The P(O)NH(CH$_2$CH$_2$OCH$_3$) linkage is referred to herein as the "MEA" linkage. Linking groups are conventionally attached to each adjacent nucleotide through an —O— linkage, but may be modified within the scope of this invention to —N— or —S—. Not all linkages in an oligomer need to be identical.

Dithioate linkages in oligonucleotides are discussed further in commonly-owned copending U.S. application Ser. No. 248,517. Formacetal linkages in oligonucleotides are discussed further in commonly-owned copending U.S. application Ser. No. 690,786. Other modified linkages in oligonucleotides are discussed further in commonly-owned copending U.S. application Ser. No. 763,130. The disclosures of each of these three applications are incorporated herein by reference.

While the randomized portions of the oligo-nucleotides synthesized by the PCR procedure described below will contain the conventional bases adenine, guanine, cytosine, and thymine or uridine, the isolated aptamers may be sequenced and resynthesized as described above. Included within the invention are synthetic procedures in which the resultant aptamers incorporate analogous forms of purines and pyrimidines.

"Analogous" forms of purines and pyrimidines are those generally known in the art, many of which are used as chemotherapeutic agents. An exemplary but not exhaustive list includes aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyl-uracil, 5-methoxyaminomethyl-2-thiouracil, beta-D-mannosylqueosine, 5-methoxyuracil, 2-methyl-thio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, 5-pentynyl-uracil and 2,6-diaminopurine. The use of uracil as a substitute base for thymine in deoxyribonucleic acid (hereinafter referred to as "dU") is considered to be an "analogous" form of pyrimidine in this invention. Other modified bases are disclosed in commonly-owned copending U.S. application Ser. No. 07/658,849.

Aptamer oligonucleotides may contain analogous forms of ribose or deoxyribose sugars that are generally known in the art. An exemplary, but not exhaustive list includes 2' substituted sugars such as 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

Although the conventional sugars and bases will be used in applying the method of the invention, substitution of analogous forms of sugars, purines and pyrimidines can be advantageous in designing the final product.

Aptamers containing the specific binding sequences discerned through the method of the invention can also be derivatized in various ways. For example, if the aptamer is to be used for separation of the target substance, conventionally the oligonucleotide will be derivatized to a solid support to permit chromatographic separation. If the oligonucleotide is to be used to label cellular components or otherwise for attaching a detectable moiety to target, the oligonucleotide will be derivatized to include a radionuclide, a fluorescent molecule, a chromophore or the like. If the oligonucleotide is to be used in specific binding assays, coupling to solid support or detectable label is also desirable. If it is to be used therapeutically, the oligonucleotide may be derivatized to include ligands which permit easier transit of cellular barriers, toxic moieties which aid in the therapeutic effect, or enzymatic activities which perform desired functions at the targeted site. The aptamer may also be included in a suitable expression system to provide for in situ generation of the desired sequence.

The oligonucleotides used as starting materials in the process of the invention to determine specific binding sequences may be single-stranded or double-stranded DNA or RNA. In the preferred embodiment of this invention, the sequences are single-stranded DNA. The use of DNA eliminates the need for conversion of RNA aptamers to DNA by reverse transcriptase prior to PCR amplification. Furthermore, DNA is less susceptible to plasma nuclease degradation than RNA. The starting material oligonucleotide will contain a randomized sequence portion, generally including from about 10 to 400 nucleotides, more preferably 20 to 100 nucleotides. The randomized sequence is flanked by primer sequences which permit the application of the polymerase chain reaction to the recovered oligonucleotide from the complex. The flanking sequences may also contain other convenient features, such as restriction sites which permit the cloning of the amplified sequence. These primer hybridization regions generally contain 10 to 30, more preferably 15 to 25, and most preferably 18 to 20, bases of known sequence.

Both the randomized portion and the primer hybridization regions of the initial oligomer population are preferably constructed using conventional solid phase techniques. Such techniques are well known in the art, such methods being described, for example, in Froehler, B., et al., *Nucleic Acids Research* (1986) 14:5399–5467; *Nucleic Acids Research* (1988) 16:4831–4839; *Nucleosides and Nucleotides* (1987) 6:287–291; Froehler, B., *Tet Lett* (1986) 27:5575–5578. Oligonucleotides may also be synthesized using solution phase methods such as triester synthesis, known in the art. For synthesis of the randomized regions, mixtures of nucleotides at the positions where randomization is desired are added during synthesis.

Any degree of randomization may be employed. Some positions may be randomized by mixtures of only two or three bases rather than the conventional four. Randomized positions may alternate with those which have been specified. Indeed, it is helpful if some portions of the candidate randomized sequence are in fact known.

While the method of the invention is illustrated using thrombin, bradykinin and PGF2α as the target substances, any biomolecule can be used as the target. Thus, other desired targets, including polypeptides, enzymes, proteins, lipids, glycolipids, phospholipids, leukotrienes, lipoproteins, glycoproteins, carbohydrates, or cell surface molecules, and more specifically thrombin and bradykinin, can be used. Target molecules that are not conventionally considered to be biomolecules are also appropriate for the methods described herein. Examples of "non-biomolecule" targets include intermediates or end-products generated by chemical synthesis of compounds used in therapeutic, manufacturing or cosmetic applications. Aptamer oligonucleotides may be used to specifically bind to most organic compounds and are suitably used for isolation or detection of such compounds.

The Method

Generally, a method for selecting aptamers is disclosed in copending application U.S. Ser. No. 07/586,769. An improved method for selecting aptamers that bind the desired target substances, involving detachment of target-aptamer complexes from column matrices, disclosed in commonly-owned copending U.S. application Ser. No. 744,870 is as follows. First, a pool of single-stranded random DNA oligomers is generated using conventional synthesis techniques. As described above, each oligomer contains both a randomized sequence as well as flanking regions of known sequence to serve as primer binding sites for PCR amplification. The synthesized single-stranded DNA pool is amplified by PCR. The amplified pool may be left as duplex DNA, or single-stranded DNA may be recovered by subsequent strand separation, and optionally transcribed into RNA.

Next, a column or other support matrix having covalently or noncovalently coupled target molecules is synthesized. Any standard coupling reagent or procedure may be utilized, depending on the nature of the support and the target molecule. For example, covalent binding may include the formation of disulfide, ether, ester or amide linkages. The length of the linkers used may be varied by conventional means. Noncovalent linkages include antibody-antigen interactions, protein-sugar interactions, as between, for example, a lectin column and a naturally-occurring oligosaccharide unit on a peptide.

Lectins are proteins or glycoproteins that can bind to complex carbohydrates or oligosaccharide units on glycoproteins, and are well-described in *The Lectins* (I. E. Liener et al., eds., Academic Press 1986). Lectins are isolated from a wide variety of natural sources, including peas, beans, lentils, pokeweed and snails. Concanavalin A is a particularly useful lectin.

Other linking chemistries are also available. For example, disulfide-derivatized biotin (Pierce) may be linked to a target molecule by coupling through an amine or other functional group. The resulting target-S-S-biotin complex could then be used in combination with avidin-derivatized support. Oligonucleotide-target complexes could then be recovered by disulfide bond cleavage. Alternatively, target may be coupled via a cis-diol linker, and oligonucleotide-target complexes may be recovered by mild oxidation of the vicinal diol bond using $NaIO_4$ or other appropriate reagents. Linking chemistries will be selected on the basis of (i) conditions or reagents necessary for maintaining the structure or activity of the target molecule, and/or (ii) chemical groups or moieties on the target molecule available for linking to the support.

Once the oligomer pool and target-coupled support have been synthesized, the oligomers are added to and incubated with the support to permit oligonucleotide-target complexation. Complexes between the oligonucleotide and target molecule are separated from uncomplexed oligonucleotides by removing unbound oligomers from the support environment. For example, if columns are used, nonbinding species are simply washed from the column using an appropriate buffer.

Following removal of unbound oligomers, the target molecules are uncoupled from the support. The uncoupling procedure depends on the nature of the coupling, as described above. Targets bound through disulfide linkages, for example, may be removed by adding a sulfhydryl reagent such as dithiothreitol or β-mercaptoethanol. Targets bound to lectin supports may be removed by adding a complementary monosaccharide (e.g., α-methyl-mannoside for concanavalin A). Oligonucleotides specifically bound to the target can then be recovered by standard denaturation techniques such as phenol extraction.

The method of elution of target-oligonucleotide complex from a support has superior unexpected properties when compared with standard oligonucleotide elution techniques. This invention is not dependent on the mechanism by which these superior properties occur. However, without wishing to be limited by any one mechanism, the following explanation is offered as to how more efficient elution is obtained. Certain support effects result from the binding of oligonucleotides to the support, or the support in conjunction with oligonucleotide or target. Removing oligonucleotide-target complexes enables the recovery of oligonucleotides specific to target only, while eliminating oligo-nucleotides binding to the support, or the support in conjunction with oligonucleotide or target. At each cycle of selection, this method may give up to 1,000-fold enrichment for specifically binding species. Selection with targets remaining bound to support gives less enrichment per cycle, making it necessary to go through many more cycles in order to get a good aptamer population.

Once oligonucleotides that bind to the target are separated from the rest of the pool and further separated from the target molecule, the oligonucleotides are amplified by PCR to give a pool of DNA sequences. The PCR method is well known in the art and described in, e.g., U.S. Pat. Nos. 4,683,195 and 4,683,202 and Saiki, R. K., et al., *Science* (1988) 239:487–491, and European patent applications 86302298.4, 86302299.2 and 87300203.4, as well as *Methods in Enzymology* (1987) 155:335–350. If RNA is initially used, the amplified DNA sequences are transcribed into RNA. The recovered DNA or RNA, in the original single-stranded or duplex form, is then used in another round of selection and amplification. After three to six rounds of selection/amplification, oligomers that bind with an affinity in the mM to $\mu$M range can be obtained for most targets and affinities below the $\mu$M range are possible for some targets. PCR may also be performed in the presence of target.

Amplified sequences can be cloned and individual oligonucleotides then sequenced. The entire process can then be repeated using the recovered and amplified oligomers as needed. Once an aptamer that binds specifically to a target has been selected, it may be recovered as DNA or RNA in single-stranded or duplex form using conventional techniques.

Similarly, a selected aptamer may be sequenced and resynthesized using one or more of the modified bases, sugars and linkages described herein using conventional techniques. Additional techniques, such as methods of synthesis of 2'-modified sugars or carbocyclic sugar analogs, are described in Sproat, B. S. et al., *Nuc Acid Res* (1991) 19:733–738; Cotten, M. et al., *Nuc Acid Res* (1991) 19:2629–2635; Hobbs, J. et al., *Biochemistry* (1973) 12:5138–5145; and Perbost, M. et al., *Biochem Biophys Res Comm* (1989) 165:742–747 (carbocyclics). Methods of synthesizing modified linkages are described in commonly-owned copending U.S. application Ser. Nos. 763,130, 248,517 (dithioates), 690,786 (formacetals), and 555,552 (amidates).

When a number of individual, distinct aptamer sequences for a single target molecule have been obtained and sequenced as described above, the sequences may be examined for "consensus sequences." As used herein, "consensus sequence" refers to a nucleotide sequence or region (which may or may not be made up of contiguous nucleotides), which is found in one or more regions of at least two aptamers, the presence of which may be correlated with aptamer-to-target-binding or with aptamer structure.

A consensus sequence may be as short as three nucleotides long. It also may be made up of one or more noncontiguous sequences with nucleotide sequences or polymers of hundreds of bases long interspersed between the consensus sequences. Consensus sequences may be identified by sequence comparisons between individual aptamer species, which comparisons may be aided by computer programs and other tools for modeling secondary and tertiary structure from sequence information. Generally, the consensus sequence will contain at least about 3 to 20 nucleotides, more commonly from 6 to 10 nucleotides.

When a consensus sequence is identified, oligonucleotides that contain that sequence may be made by conventional synthetic or recombinant means. These aptamers, termed "secondary aptamers," may also function as target-specific aptamers of this invention. A secondary aptamer may conserve the entire nucleotide sequence of an isolated aptamer, or may contain one or more additions, deletions or substitutions in the nucleotide sequence, as long as a consensus sequence is conserved. A mixture of secondary aptamers may also function as target-specific aptamers, wherein the mixture is a set of aptamers with a portion or portions of their nucleotide sequence being random or varying, and a conserved region which contains the consensus sequence. Additionally, secondary aptamers may be synthesized using one or more of the modified bases, sugars and linkages described herein using conventional techniques and those described herein.

Aptamers can also be selected using a pool of oligonucleotides that vary in length as the starting material. Thus, several pools of random sequence-containing oligonucleotides that vary in length from, e.g., 10 to 400 bases, and contain the same flanking primer-binding sequences, are synthesized. Equimolar amounts of each pool are mixed and the variable-length pool is then used to select for aptamers that bind to the desired target substance, as described above. This protocol selects for the optimal species for target binding from the starting pool and does not limit aptamers to those of one given length.

Alternatively, several pools of mixed length aptamers can be used in parallel in separate selections and then combined and further selected to obtain the optimal binders from the size range initially used. For example, three pools, A, B and C, can be used. Pool A can consist of oligonucleotides having random sequences that vary in length from 30 to 40 bases; pool B can have sequences varying in length from 40 to 50 bases; and pool C can have sequences varying in length from 50 to 60 bases. It is to be understood that the lengths described above are for illustrative purposes only. After selection to obtain binders from A, B, and C, the selected oligonucleotides are mixed together. A number of rounds of selection are done as described above to obtain the best binders from the initial species selected in the 30- to 60-base range.

It is pointed out that copending, commonly assigned U.S. application Ser. No. 07/659,980 discloses methods for isolating aptamers that have no known flanking sequences. The above-referenced U.S. Patent Application is incorporated herein by reference for disclosing such methodology. Such amplification methods may be used in combination with the methods disclosed in the present application.

Utility of the Retrieved Sequence

The aptamers of the invention are useful in diagnostic, research and therapeutic contexts. For diagnostic applications, these aptamers are particularly well suited for binding to biomolecules that are identical or similar between different species, where standard antibodies may be difficult to obtain. They are also useful in inhibition assays when the aptamers are chosen to inhibit the biological activity of its target. Antibodies are generally used to bind analytes that are detected or quantitated in various diagnostic assays. Aptamers represent a class of molecules that may be used in place of antibodies for in vitro or in vivo diagnostic and purification purposes.

The aptamers of the invention are therefore particularly useful as diagnostic reagents to detect the presence or absence of the target substances to which they specifically bind. Such diagnostic tests are conducted by contacting a sample with the specifically binding oligonucleotide to obtain a complex which is then detected by conventional means. For example, the aptamers may be labeled using radioactive, fluorescent, or chromogenic labels and the presence of label bound to solid support to which the target substance has been bound through a specific or nonspecific binding means detected. Alternatively, the specifically binding oligonucleotides may be used to effect initial complexation to the support. Means for conducting assays using such oligomers as specific binding partners will track those for standard specific binding partner based assays.

It may be commented that the mechanism by which the specifically binding oligomers of the invention interfere with or inhibit the activity of a target substance is not always established, and is not a part of the invention. The oligomers of the invention are characterized by their ability to bind specific target molecules regardless of the mechanisms of binding or the mechanism of the effect thereof.

For use in research or manufacturing, the specifically binding oligonucleotides of the invention are especially helpful in effecting the isolation and purification of substances to which they bind. For this application, typically, the aptamer containing the specific binding sequences is conjugated to a solid support and used as an affinity ligand in chromatographic separation of the target substance.

In therapeutic applications, the aptamers of the invention can be formulated for a variety of modes of administration, including systemic and topical or localized administration. Techniques and formulations generally may be found in *Remington's Pharmaceutical Sciences*, Mack Publishing Co., Easton, Pa., latest edition. In general, the dosage required for therapeutic efficacy will range from about 0.1 μg to 20 mg aptamer/kg body weight. Alternatively, dosages within these ranges can be administered by constant infusion over an extended period of time, usually exceeding 24 hours, until the desired therapeutic benefits have been obtained.

For systemic administration, injection is preferred, including intramuscular, intravenous, intraperitoneal, and subcutaneous. For injection, the aptamers of the invention are formulated in liquid solutions, preferably in physiologically compatible buffers such as Hank's solution or Ringer's solution. In addition, the aptamers may be formulated in solid form and redissolved or suspended immediately prior to use. Lyophilized forms are also included.

Systemic administration can also be by transmucosal or transdermal means, or the oligomers can be administered orally. Additional formulations which are suitable for other modes of administration include suppositories, intranasal and other aerosols. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

The aptamers may also be employed in expression systems, which are administered according to techniques applicable, for instance, in applying gene therapy.

The following examples are meant to illustrate, but not to limit the invention.

EXAMPLE 1
Synthesis of oligonucleotide Pool

DNA oligonucleotides containing a randomized sequence region were synthesized using standard solid phase techniques and phosphoramidite chemistry (oligonucleotide Synthesis, Gait, M. J., ed. (IRL Press), 1984; Cocuzza, A., *Tetrahedron Letters*, (1989) 30:6287–4610–0032.21 6291). A 1 µM small-scale synthesis yielded 60 nmole of HPLC-purified single-stranded randomized DNA. Each strand consisted of specific 18-mer sequences at both the 5' and 3' ends of the strand and a random 60-mer sequence in the center of the oligomer to generate a pool of 96-mers with the following sequence (N =G, A, T or C):

5' HO—CGTACGGTCGACGCTAGCN$_{60}$CACGTGGAGCTCGGATCC—OH 3' (SEQ ID NO:1)

DNA 18-mers with the following sequences were used as primers for PCR amplification of oligonucleotide sequences recovered from selection columns. The 5' primer sequence was 5' HO-CGTACGGTCGACGCTAGC-OH 3' (SEQ ID NO:2 ) and the 3' primer sequence was 5' biotin-O-GGATCCGAGCTCCACGTG-OH 3' (SEQ ID NO:3 ). The biotin residue was linked to the 5' end of the 3' primer using commercially available biotin phosphoramidite (New England Nuclear, Cat. No. NEF-707). The biotin phosphoramidite is incorporated into the strand during solid phase DNA synthesis using standard synthesis conditions.

In another, similar experiment, a pool of 98-mers with the following sequence was synthesized:

5' HO—AGAATACTCAAGCTTGCCG—N$_{60}$—ACCTGAATTCGCCCTATAG—OH 3' (SEQ ID NO:4).

DNA 19-mers with the following sequences can also be used as primers for PCR amplification of oligonucleotides recovered from selection columns. The 3' primer sequence is 5' biotin—O—CTATAGGGCGAATTCAGGT—OH 3' (SEQ ID NO:5)

and the 5' primer sequence is

5' HO—AGAATACTCAAGCTTGCCG—OH 3' (SEQ ID NO:6).

It will be noted that in all cases, the duplex form of the primer binding sites contain restriction enzyme sites.

EXAMPLE 2
Isolation of Thrombin Aptamers Using Thrombin Immobilized on a Lectin Column A pool of aptamer DNA 96 bases in length was synthesized as described in Example 1, and then PCR-amplified to construct the initial pool. A small amount of the enzymatically-synthesized DNA was further amplified in the presence of α-$^{32}$P-dNTPs to generate labeled aptamer to permit quantitation from column fractions.

A thrombin column was prepared by washing 1 ml (58 nmole) agarose-bound concanavalin A ("Con-A") (Vector Laboratories, cat. no. AL-1003) with 20 mM Tris-acetate buffer (pH 7.4) containing 1 mM MgCl$_2$, 1 mM CaCl$_2$, 5 mM KCl and 140 mM NaCl (the "selection buffer") (4×10 ml). 1 ml of settled support was then incubated overnight at 4° C. in 10 ml selection buffer containing 225 µg (6.25 nmole) thrombin (Sigma, Cat. no. T-6759). After shaking overnight to permit thrombin binding to the Con-A beads, the mixture was briefly centrifuged and the supernatant removed. The beads were resuspended in fresh selection buffer and transferred to a column which was then washed with selection buffer (5×1 ml). A column containing 1 ml of settled beads had a void volume of approximately 300 µL. A control Con-A column was prepared by adding 1 ml of settled support to a column followed by 5 washes of 1 ml of selection buffer.

Prior to application of the aptamer DNA pool to Con-A columns, the DNA was heated in selection buffer at 95° C. for 3 minutes and then cooled on ice for 10 minutes. The pool, consisting of 100 pmole DNA in 0.5 ml selection buffer, was then pre-run on the control Con-A column at room temperature to remove species that bound to the control support. Three additional 0.5 ml aliquots of selection buffer were added and column fractions 2, 3 and 4 (0.5 ml each) were pooled and then reapplied to the column twice. The DNA in 1.5 ml selection buffer was then recovered. Approximately 1% of total input cpm were retained on the column.

The recovered DNA was then applied to a Con-A-thrombin column as a 0.5 ml aliquot followed by a 1.0 ml aliquot. Flow-through was retained and reapplied to the column twice. DNA added to the column on the final application was left on the column for 1 hour at room temperature. The column was then eluted with 0.5 ml aliquots of selection buffer. 0.5 ml fractions were collected and radioactivity was determined in each fraction. Radioactivity in eluted fractions 7 through 12 were low and relatively constant. After recovery of fraction 12, the column was washed with 0.5 ml aliquots of 0.1M α-methylmannoside (Sigma Cat. no. M-6882) in selection buffer to elute the bound thrombin along with thrombin-bound aptamers. Fractions 14 and 15 showed a significant peak of thrombin enzyme activity, as determined spectrophotometrically by conversion of a chromogenic substrate (Kabi Diagnostica, Cat. no. S-2238). 0.01% of the input DNA eluted in these two fractions.

Aptamer DNA (Round 1 DNA) was recovered from the thrombin by phenol extraction (2×0.5 ml). The aqueous phase volume was reduced to about 250 µl by n-butanol extraction. Aptamer DNA was precipitated on dry ice using 3 volumes of ethanol and 20 µg of glycogen as a carrier. The DNA was pelleted, washed once in 70% ethanol and then dried.

EXAMPLE 3
Amplification of Selected Aptamers

Round 1 DNA from Example 2 was resuspended in 100 µl of H$_2$O and amplified by PCR. A 200 µl PCR reaction consisted of the following: 100 µl template 96-mer DNA (approximately 0.01 pmoles); 20 µl 10X buffer (100 mM Tris-Cl (pH 8.3), 500 mM KCl, 20 mM MgCl$_2$); 32 µl dNTP's (5 mM conc total, 1.25 mM each dATP, dCTP, dGTP, and dTTP); 20 µl primer 1 (biotinylated 18-mer, 50

µM); 20 µl primer 2 (18-mer, 50 µM); 6µl α-$^{32}$P-dNTP's (approximately 60 µCi); and 2 µl Taq I Polymerase (10 units). The reaction was covered with 2 drops NUJOL mineral oil. A control reaction was also performed without template aptamer.

Initial denaturation was at 94° C. for 3 minutes, but subsequent denaturation after each elongation reaction lasted 1 minute. Primer annealing occurred at 60° C. for 1 minute, and elongation of primed DNA strands using the Taq polymerase ran at 72° C. for 2 minutes, with 5-second extensions added at each additional cycle. The final elongation reaction to completely fill in all strands ran for 10 minutes at 72° C., and the reaction was then held at 4° C.

18 rounds of Taq polymerase elongation were carried out in order to amplify the selected aptamer DNA. After the reactions were completed, the aqueous layer was retrieved and any residual NUJOL oil was removed by n-butanol extraction, reducing the volume to 100 µl. A sample may be removed from each of the aptamer and control reaction for quantitation and analytical PAGE. The amplified aptamer pool (100 µl) was run over a Nick column (G-50 Sephadex, washed with 3 ml TE buffer (10 mM Tris-HCl (pH 7.6), 0.1 mM EDTA)) to remove unincorporated NTP's, primers, and salt. 400 µl of TE buffer was then added to the column and the DNA pool was eluted from the column with an additional 400 µl using TE buffer. (A sample may be removed from the eluent for quantitation and analytical PAGE.) The eluent (400 µl) was loaded on an avidin agarose column (Vector Laboratories, Cat. No. A-2010) (500 µl settled support, washed with 3×1 ml Tris/NaCl buffer (0.1M Tris, 0.1M NaCl, pH 7.5)). Approximately 90% of the loaded radioactivity remained on the column. The column was washed with Tris/NaCl buffer (4×400 µl) and then the nonbiotinylated strand was eluted with 0.15N NaOH (3×300 µl fractions). More than 45% of the radioactivity on the column eluted in these three fractions. These fractions (900 µl) were combined and neutralized with approximately 3.5 µl of glacial acetic acid. The neutralized fractions were reduced to 250 µl by speed vacuum or butanol extraction and the nucleic acids were precipitated with EtOH. The resultant pellet was dissolved in 102 µl selection buffer. A 2 µl sample was removed for quantitation and analytical PAGE. The resulting amplified Round 1 Pool was applied to a new Con-A-thrombin column as in Example 2 to obtain Round 2 aptamers.

EXAMPLE 4

Characterization of Round 1 Through Round 5 Aptamers Obtained from Selection on Lectin Columns Five rounds of thrombin aptamer selection and amplification were carried out using Con-A-thrombin columns as in Examples 2 and 3. As shown in Table 2, the combined fractions 14 and 15 contained a maximum of about 10% of input DNA using the described conditions.

TABLE 2

| Round | % DNA eluted by α-methyl-mannoside* | % DNA bound to control support |
|---|---|---|
| 1 | 0.01 | 0.7 |
| 2 | 0.055 | 1.9 |
| 3 | 5.80 | 2.3 |

TABLE 2-continued

| Round | % DNA eluted by α-methyl-mannoside* | % DNA bound to control support |
|---|---|---|
| 4 | 10.25 | 1.1 |
| 5 | 9.70 | 1.0 |

*0.1 M α-methyl-mannoside in selection buffer was added as fraction 13 in each elution, and fractions 14 and 15 were retained and the DNA amplified. Due to slow leeching of thrombin from the column, DNA bound to thrombin could also be seen in earlier fractions in rounds 3–5.

After amplification, round 5 aptamer DNA was analyzed for specificity in a filter binding assay. In this assay, nitrocellulose filters (1 cm diameter) prebound with salmon sperm DNA were used to bind either: (1) An unselected 96-mer oligonucleotide DNA pool, (2) unselected DNA with thrombin (60 pmole), (3) Round 5 aptamer DNA and thrombin (60 pmole), (4) Round 5 aptamer DNA alone, or (5) Round 5 aptamer DNA and ovalbumin (60 pmole). In each case 3.5 pmole of DNA was used and the incubation was in 200 µL selection buffer at room temperature for 1 hour. The filters were then washed 3 times with 3.0 ml of selection buffer and radioactivity was counted to determine the amount of DNA that was retained as a thrombin complex. The results are shown in Table 3.

TABLE 3

| DNA | % DNA Bound to Filter |
|---|---|
| Unselected 96-iner | 0.08 |
| Unselected 96-mer + thrombin | 0.06 |
| Round 5 aptamer + thrombin | 20.42 |
| Round 5 aptamer | 0.07 |
| Round 5 aptamer + ovalbumin | 0.05 |

Unselected DNA did not show significant binding to the thrombin while selected aptamer DNA bound to thrombin. Binding results show specific thrombin binding with no detectable ovalbumin binding.

Round 5 aptamer DNA was then amplified using the following 3' primer sequence:

5' HO—TAATACGACTCACTATAGGGATCCGAGCTCCACGTG—OH 3' (SEQ ID NO:7)

and the 5' 18-mer primer sequence shown in Example 1. The 36-mer primer was used to generate internal BamHl restriction sites to aid in cloning. The amplified Round 5 aptamer DNA was then cloned into PGEM 3Z (Promega). 32 of the resulting clones were then amplified directly using the following 5' primer sequence:

5' HO—CTGCAGGTCGACGCTAGC—OH 3' (SEQ ID NO:8)

and the 3' biotinylated 18-mer primer sequence shown in Example 1, and then sequenced.

Filter binding assays using aptamer DNA from 14 of the clones were used to determine the dissociation constants ($K_D$) for thrombin as follows: Thrombin concentrations between 10 µM and 1 nM were incubated at room temperature in selection buffer for 5 minutes in the presence of 0.08 pmole of radiolabeled 96-mer derived from cloned Round 5 aptamer DNA. After incubation, the thrombin and aptamer mixture was applied to nitrocellulose filters (0.2 micron, 2.4 cm diameter) that were pretreated with salmon sperm DNA (1 mg/ml DNA in selection buffer) and washed twice with 1 ml selection buffer. After application of thrombin mixture, the filters were washed three times with 1 ml selection buffer The radioactivity retained on the filters was then determined. $K_D$ values for the individual clones ranged from 50 to >2000 nM.

The DNA sequence of the 60-nucleotide randomly-generated region from 32 clones was determined in order to examine both the heterogeneity of the selected population and to identify homologous sequences. Sequence analysis showed each of the 32 clones to be distinct. However, striking sequence conservation was found. The hexamer 5' GGTTGG 3' (SEQ ID NO:9) was found at a variable location within the random sequence in 31 of 32 clones, and five of the six nucleotides are strictly conserved in all 32. Additionally, in 28 of the 32 clones a second hexamer 5' GGNTGG 3' (SEQ ID NO:10), where N is usually T and never C, is observed within 2–5 nucleotides from the first hexamer. Thus, 28 clones contain the consensus sequence 5' GGNTGG(N)$_z$GGNTGG 3' (SEQ ID NO:11) (SEQ ID NO:12) (SEQ ID NO:13) (SEQ ID NO:14) where z is an integer from 2 to 5. The remaining 4 clones contain a "close variant sequence" (a sequence differing by only a single base). A compilation of the homologous sequences are shown in FIG. 1. It should be noted that DNA sequencing of several clones from the unselected DNA population or from a population of aptamers selected for binding to a different target revealed no homology to the thrombin-selected aptamers. From these data we conclude that this consensus sequence contains a sequence which is responsible either wholly or in part, for conferring thrombin affinity to the aptamers.

Clotting time for the thrombin-catalyzed conversion of fibrinogen (2.0 mg/ml in selection buffer) to fibrin at 37° C. was measured using a precision coagulation timer apparatus (Becton-Dickinson, Cat. Nos. 64015, 64019, 64020). Thrombin (10 nM) incubated with fibrinogen alone clotted in 40 sec, thrombin incubated with fibrinogen and P1 nuclease (Boehringer-Mannheim, Indianapolis, Ind.) clotted in 39 sec, thrombin incubated with fibrinogen and aptamer clone #5 (200 nM) clotted in 115 sec, and thrombin incubated with fibrinogen, clone #5 (200 nM) and P1 nuclease clotted in 40 sec. All incubations were carried out at 37° C. using reagents prewarmed to 37° C. Aptamer DNA or, when present, P1 nuclease, was added to the fibrinogen solution prior to addition of thrombin. These results demonstrated that (i) thrombin activity was inhibited specifically by intact aptamer DNA and (ii) that inhibitory activity by aptamer did not require a period of prebinding with thrombin prior to mixing with the fibrinogen substrate.

Inhibition of thrombin activity was studied using a consensus-related sequence 7-mer, 5' GGTTGGG 3' (SEQ ID NO:15), or a control 7-mer with the same base composition but different sequence (5' GGGGGTT 3' ) (SEQ ID NO:16). Clotting times were measured using the timer apparatus as above. The thrombin clotting time in this experiment was 24 sec using thrombin alone (10 nM), 26 sec with thrombin and the control sequence at 20 $\mu$M and 38 sec with thrombin plus the consensus sequence at 20 $\mu$M, indicating specificity for thrombin inhibition at the level of the 7-mer.

The inhibitory aptamers were active at physiological temperature under physiologic ion conditions and were able to bind to thrombin in the presence of the fibrinogen substrate, a key requirement for therapeutic efficacy.

EXAMPLE 5
Selection for Aptamers That Interfere With Biological Function one skilled in the art may apply these teachings to identify aptamers that may have desirable functional attributes, e.g., capacity to inhibit enzyme activity. In the context of the present example with thrombin, an immobilized column wherein the thrombin is attached covalently or noncovalently (e.g., using avidin/biotin) may be used essentially as described in Example 7. However, the aptamers may be eluted by adding substrate to the column. Those aptamers so eluted by thrombin substrate are presumably displaced by competition and thus may be binding to the same region of the protein. This example may be applicable to the isolation of aptamers that can be displaced by antibodies (where the site is known) or by a cognate receptor molecule, e.g., interleukin I may be used to displace aptamers which bind to the interleukin I receptor.

EXAMPLE 6
Selection for Aptamers to Bradykinin

SPDP (Pharmacia, 60 mg, 192 $\mu$mole) was dissolved in EtOH (6 ml) and added in 1 ml aliquots with stirring to bradykinin (Bachem, 213 mg, 157 $\mu$mole) in buffer (20 ml, 100 mM NaH$_2$PO$_4$, 100 mM NaCl, pH 7.5). After shaking the reaction for 1 hour at room temperature, dithiothreitol (DTT, 1M, 1.35 ml) was added and the reaction was shaken for an additional hour at room temperature. The thiolated bradykinin was purified by HPLC Dynamax C18 (Rainin, Emeryville, Calif.). Thiopropylbradykinin in 10 ml buffer (100 mM Tris-Cl, pH 7.6, 500 mM NaCl, 1 mM EDTA) was then added to 12 ml of thiol activated Sepharose 6B support (Pharmacia) equilibrated in buffer. The mixture was shaken for 2 hours at room temperature and then washed over a frit with double-distilled water. The amount of bradykinin loading was estimated by determining the concentration of pyridine-2-thione released (A$_{343}$nm=8.08×10$^3$ M$^{-1}$, cm$^{-1}$). Approximately 12.5 $\mu$moles bradykinin per ml support was obtained, giving a 94% overall yield.

The bradykinin column was characterized for its performance with regard to release of bradykinin mediated by 100 mM dithiothreitol (DTT) in selection buffer. It was found that after addition of DTT, disulfide-linked bradykinin (i.e., bradykinin-NH-CO-CH$_2$-CH$_2$-SH) was immediately released from the column matrix and eluted in the fraction following the void volume. This was true of both a column consisting only of bradykinin and a column consisting of bradykinin with bound round 5 aptamer DNA (prepared in the same procedure of Examples 2 and 3 except using a bradykinin column and eluting with DTT instead of $\alpha$-methyl-mannoside). The presence of bound bradykinin aptamer DNA thus did not interfere with release of bradykinin from the column after DTT was added.

Release of bradykinin from the column was monitored by analysis of the eluted fraction after addition of DTT. Fractions (about 300 $\mu$L) were extracted in n-butanol and the bradykinin present in the butanol was detected by HPLC. The column fractions were run over a HPLC Dynamax C18 column using an aqueous solvent containing 0.1% trifluoroacetic acid and an acetonitrile gradient (1% to 50% over 30 minutes) at a flow rate of 1 ml/minute (37° C.). Thiol-linkered bradykinin from either column eluted at 22 minutes while native bradykinin eluted at 20 minutes.

Round 5 aptamers for bradykinin prepared by this method had a K$_D$ of 50 $\mu$M, as compared to a K$_D$ of >1 mM for unselected DNA. The sequence of one cloned round 5 bradykinin aptamer is as follows: 5' TGCGGGC-CCCTAACTCTTTACCATGGTTCAGT-TAATAACATTAATGCT CTTTTCTCAGCC 3' (SEQ ID NO:17).

EXAMPLE 7
Selection for Aptamers to PGF2a

200 $\mu$l derivatized Toyopearl support containing 2 gmole of PGF2$\alpha$ ligand was loaded on a 1.5 ml column housing.

The column was washed with 3 ml of 20mM Tris-acetate buffer (pH 7.4) containing 1mM $MgCl_2$, 1 mM $CaCl_2$, 5mM KCl and 140 mM NaCl (the "selection buffer"). An identical column was prepared using the underivatized Toyopearl control support described in Example 1.

0.5 nmoles of the oligonucleotide pool prepared in Example 7 (doped with tracer amounts of 5'-$^{32}$P-labeled species) was resuspended in 400 µl of selection buffer and heat denatured for 2 min at 95° C. The denatured DNA was immediately transferred to wet ice for 10 min. This material was applied to the control support (underivatized Toyopearl), flow initiated, and eluent collected. Flow-through was reapplied three times. At the end of the third application, the column was rinsed with 200 µl selection buffer (1 bed volume). The flow-through was pooled and applied for a fourth time. A column profile was established using $^{32}$p quantification via Cerenkov counting. Flow-through material was then pooled for application to the PGF2α support.

Application of the flow-through pool to PGF2α-derivatized Toyopearl was performed as described above. After the third application, the column was washed with 200 µl of selection buffer and the material reapplied to establish a column profile. The support was washed with additional selection buffer until the eluting $^{32}$p material decreased to less than 0.2% of initial input cpm. The support was then washed with 1ml of selection buffer containing 1M NaCl. Bound oligonucleotides were eluted with 20mM EDTA/60% acetonitrile. The solvent was removed under vacuum and the material chromatographed on a Nick column (Pharmacia, G-50 Sephadex columns) as per the manufacturer's instructions using 10mM Tris (pH 7.5)/0.1mM EDTA/250mM NaCl. The $^{32}$P-containing fraction was then precipitated with 20 µg of carrier glycogen and absolute ethanol (2.5 vol) on dry ice for 15 minutes. The DNA was pelleted for 15 minutes at 4° C., washed with 70% ethanol, and dried under vacuum.

Further rounds of selection, amplification and purification were performed for PGF2α as for thrombin in Examples 2 and 3.

The recovery of specifically-binding oligonucleotides in each amplified pool from round 4, 5 and 6 selections remained constant at about 17% of total input cpm. Aptamers obtained from the round 6 column washes prior to addition of $CH_3CN$/EDTA were recovered by ethanol precipitation, pooled, and subjected to selection on a new PGF2α column. The total cpm recovered from $CH_3CN$/EDTA elution was about 17%.

This demonstrates that the aptamers eluted by $CH_3CN$/EDTA in round 6 specifically bind to the PGF2α ligand. The round 6 pool was further characterized by adding 1 ml of a 2.4 mg/ml solution (5 µmole) of PGF2α in selection buffer to an aptamer-bound PGF2α column (containing 2 µmole of matrix-bound PGF2α) to result in complete elution of bound aptamer. This result shows ligand-specific elution of the pool, a common property of affinity-selected ligands. See Schott, H., *Affinity Chromatography*, (Marcel Dekker, Inc., New York, 1984).

The sequence of one 60-base region of a 96-mer PGF2α aptamer is as follows:

The underlined regions may be consensus sequences.

EXAMPLE 8
Thrombin Aptamer Pharmacokinetic Studies

A 15-mer single-stranded deoxynucleotide, 5' GGTTG-GTGTGGTTGG 3' (SEQ ID NO:19), identified as a consensus sequence from 30 thrombin aptamer clones as described in Example 4 above was used. Young adult rats of mixed gender and strain were used. The animals were anesthetized and a diester of the 15-mer was injected through a catheter in 200 µl volumes (in 20 mM phosphate buffer, pH 7.4, 0.15M NaCl) at two concentrations, so that the final concentration of 15-mer in the blood was about 0.5 and 5.0 µM respectively, although the exact concentration depends on the volume of distribution which is unknown for this oligonucleotide. These values are 10 to 100 times greater than the human in vitro $K_d$ value. No heparin was used for catheterization.

At 0, 5, 20 and 60 minutes, blood was withdrawn from the animals (approx. 500 µl aliquots) and transferred into tubes containing 0.1 volume citrate buffer and centrifuged. Rat plasma was removed and tested in a thrombin clotting-time assay. Six animals were used at each concentration, and three animals were injected with the control carrier solution containing no 15-mer.

A prolonged clotting time was observed at the 5 minute time point at both concentrations, with the most significant prolongation occurring at the higher dose concentration. Little or no activity was observed at 20 minutes. Thus, the 15-mer in blood withdrawn from rats 5 minutes post-injection was able to inhibit exogenously added human thrombin. A separate APTT test at the 5 minute time point showed that the 15-mer also inhibited rat blood coagulation, presumably by inhibiting rat thrombin to a significant degree. The half-life of the 15-mer in rats appears to be about 5 minutes or less.

EXAMPLE 9
Thrombin Aptamer Analogs

Analogs to the single-stranded, thrombin consensus sequence-containing deoxynucleotide 15-mer described in Example 8, 5' GGTTGGTGTGGTTGG 3', and a closely related 17-mer, were synthesized using conventional techniques. These analogs for the most part contain the identical nucleotide sequences, bases, sugars and phosphodiester linkages, but substitute one or more modified linking groups (thioate or MEA), or modified bases (uracil or 5-pentynyluracil).

The inhibition constants ($K_i$s) and mode of inhibition of the aptamer analogs were determined through steady-state inhibition kinetics using a clotting time assay with constant thrombin concentration and varying the fibrinogen concentration in the presence of aptamer, control DNA, or no DNA. The data shown in Table 4 lists $K_i$ values ranging from about 15 to 280 nM. The data is consistent with a non-competitive mode of inhibition.

Independent verification of the $K_i$ for the nonmodified 15-mer was made by determining the extent of thrombin inhibition with varying DNA concentration. The data revealed 50% inhibition of thrombin activity at approximately the same concentration as the derived $K_i$, strongly suggesting that each bound thrombin was largely, if not 5' CTGCCGCGTTCCTCACTTC<u>TTGCT</u>GCACATTTTCAGTGCACACGGAGG<u>CTATT</u>CGCTCGA 3' (SEQ ID NO:18).

completely, inhibited, and that binding occurred with a 1:1 stoichiometry.

TABLE 4

| Compound | $K_i$ (nM) |
|---|---|
| GGTTGGTGTGGTTGG (SEQ ID NO:14) | 20 |
| GGTTGGTGTGGTTGG#G#T (SEQ ID NO:20) | 35 |
| GGTTGGTGTGGTT*G*G (SEQ ID NO:21) | 40 |
| G*G*T*T*G*G*T*G*T*G*G*T*T*G*G (SEQ ID NO:22) | 280 |
| GGTTGG(dU)G(dU)GGTTGG (SEQ ID NO:23) | 15 |

TABLE 4-continued

| Compound | $K_i$ (nM) |
|---|---|
| GG(dU)TGGTGTGG(dU)TGG (SEQ ID NO:24) | 80 |
| GGTTGGTGTGGTU'GG (SEQ ID NO:25) | 20 |

*indicates a thioate (i.e., P(O)S) linkage
# indicates a MEA linkage
U' indicates 5-pentynyluracil

We claim:

1. A composition consisting essentially of the aptamer having the formula:
GGTTGGTGTGGTTGG (SEQ ID NO:19),
GGTTGGTGTGGTTGG#G#T (SEQ ID NO:20),
GGTTGGTGTGGTT*G*G (SEQ ID NO:21),
G*G*T*T*G*G*T*G*T*G*G*T*T*G*G (SEQ ID NO:22),
GGTTGG(dU)G(dU)GGTTGG (SEQ ID NO:23),
GG(dU)TGGTGTGG(dU)TGG (SEQ ID NO:24), or
GGTTGGTGTGGTU' GG (SEQ ID NO:25);
wherein:
* indicates a P(O)S linkage,
# indicates a P(O)NH(CH$_2$CH$_2$OCH$_3$) linkage, and
U' indicates 5-(1-pentynyl)uracil.

2. The composition of claim 1 wherein the composition consists essentially of the aptamer having formula GGTTGGTGTGGTTGG (SEQ ID NO:19).

3. An aptamer capable of binding specifically to thrombin, wherein the aptamer is selected from the group consisting of:
GGTTGGTGTGGTTGG (SEQ ID NO:19),
GGTTGGTGTGGTTGG#G#T (SEQ ID NO:20),
GGTTGGTGTGGTT*G*G (SEQ ID NO:21),
G*G*T*T*G*G*T*G*T*G*G*T*T*G*G (SEQ ID NO:22),
GGTTGG(dU)G(dU)GGTTGG (SEQ ID NO:23),
GG(dU)TGGTGTGG(dU)TGG (SEQ ID NO:24), or
GGTTGGTGTGGTU' GG (SEQ ID NO:25);
wherein:
* indicates a P(O)S linkage,
# indicates a P(O)NH(CH$_2$CH$_2$OCH$_3$) linkage, and
U' indicates 5-(1-pentynyl)uracil.

4. The aptomer of claim 4 wherein the aptamer is of the formula GGTTGGTGTGGTTGG (SEQ ID NO:19).

* * * * *

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGTACGGTCG ACGCTAGCNN NNNNNNNNNN NNNNNNNNNN NNNNNNNNNN NNNNNNNNNN  60

NNNNNNNNNN NNNNNNNNCA CGTGGAGCTC GGATCC  96

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CGTACGGTCG ACGCTAGC  18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGATCCGAGC TCCACGTG  18

( 2 ) INFORMATION FOR SEQ ID NO:4:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AGAATACTCA AGCTTGCCGN NNNNNNNNN NNNNNNNNN NNNNNNNNN NNNNNNNNN        60

NNNNNNNNN NNNNNNNNA CCTGAATTCG CCCTATAG        98

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CTATAGGGCG AATTCAGGT        19

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AGAATACTCA AGCTTGCCG        19

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TAATACGACT CACTATAGGG ATCCGAGCTC CACGTG        36

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CTGCAGGTCG ACGCTAGC        18

( 2 ) INFORMATION FOR SEQ ID NO:9:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GGTTGG        6

( 2 ) INFORMATION FOR SEQ ID NO:10:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GGNTGG                                                                                    6

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGNTGGNNGG NTGG                                                                           14

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGNTGGNNNG GNTGG                                                                          15

( 2 ) INFORMATION FOR SEQ ID NO:13:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GGNTGGNNNN GGNTGG                                                                         16

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GGNTGGNNNN NGGNTGG                                                                        17

( 2 ) INFORMATION FOR SEQ ID NO:15:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GGTTGGG                                                                                   7

( 2 ) INFORMATION FOR SEQ ID NO:16:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GGGGGTT                                                                                                                7

(2) INFORMATION FOR SEQ ID NO:17:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:17:

TGCGGGCCCC TAACTCTTTA CCATGGTTCA GTTAATAACA TTAATGCTCT TTTCTCAGCC        60

(2) INFORMATION FOR SEQ ID NO:18:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:18:

CTGCCGCGTT CCTCACTTCT TGCTGCACAT TTTCAGTGCA CACGGAGGCT ATTCGCTCGA        60

(2) INFORMATION FOR SEQ ID NO:19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:19:

GGTTGGTGTG GTTGG                                                        15

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(15..16, "")
        (D) OTHER INFORMATION: /note= "This indicates MEA
            linkage."

(ix) FEATURE:
        (A) NAME/KEY: misc_difference
        (B) LOCATION: replace(16..17, "")
        (D) OTHER INFORMATION: /note= "This indicates MEA
            linkage."

(xi) SEQUENCE DESCRIPTION: SEQ ID NO:20:

GGTTGGTGTG GTTGGGT                                                      17

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(13..14, "")
        (D) OTHER INFORMATION: /note= "This indicates a thioate (i.e., P(O)S) linkage."

( i x ) FEATURE:
    ( A ) NAME/KEY: misc_difference
    ( B ) LOCATION: replace(14..15, "")
    ( D ) OTHER INFORMATION: /note= "This indicates a thioate (i.e., P(O)S) linkage."

( x i ) SEQUENCE DESCRIPTION: SEQ ID NO:21:

GGTTGGTGTG GTTGG                    15

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1..15, "")
        ( D ) OTHER INFORMATION: /note= "These positions have
                thioate (i.e., P(O)S) linkages."

( x i ) SEQUENCE DESCRIPTION: SEQ ID NO:22:

GGTTGGTGTG GTTGG                    15

( 2 ) INFORMATION FOR SEQ ID NO:23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 7
        ( D ) OTHER INFORMATION: /note= "N is uracil as a substitute
                base for thymine in deoxyribonucleic a..."

( i x ) FEATURE:
        ( A ) NAME/KEY: misc_feature
        ( B ) LOCATION: 9
        ( D ) OTHER INFORMATION: /note= "N is uracil as a substitute
                base for thymine in deoxyribonucleic a..."

( x i ) SEQUENCE DESCRIPTION: SEQ ID NO:23:

GGTTGGNGNG GTTGG                    15

( 2 ) INFORMATION FOR SEQ ID NO:24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 3
        ( D ) OTHER INFORMATION: /note= "N is uracil as a substitute
                base for thymine in deoxyribonucleic a..."

( i x ) FEATURE:
        ( A ) NAME/KEY: misc_feature
        ( B ) LOCATION: 12
        ( D ) OTHER INFORMATION: /note= "N is uracil as a substitute
                base for thymine in deoxyribonucleic a..."

( x i ) SEQUENCE DESCRIPTION: SEQ ID NO:24:

GGNTGGTGTG GNTGG                                                                                    15

( 2 ) INFORMATION FOR SEQ ID NO:25:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 13
        ( D ) OTHER INFORMATION: /note= "N indicates
            5- pentynyluracil"

( x i ) SEQUENCE DESCRIPTION: SEQ ID NO:25:

GGTTGGTGTG GTNGG                                                                                    15

( 2 ) INFORMATION FOR SEQ ID NO:26:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 3
        ( D ) OTHER INFORMATION: /note= "N is T, A, U, dU (i.e.,
            uracil as a substitute base for thymine in
            deoxyribonucleic acid) or G."

( x i ) SEQUENCE DESCRIPTION: SEQ ID NO:26:

GGNTGG                                                                                              6

( 2 ) INFORMATION FOR SEQ ID NO:27:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 3
        ( D ) OTHER INFORMATION: /note= "N is T, A, U, dU (i.e.,
            uracil as a substitute base for thymine in
            deoxyribonucleic acid) or G."

( i x ) FEATURE:
        ( A ) NAME/KEY: misc_feature
        ( B ) LOCATION: 7..8
        ( D ) OTHER INFORMATION: /note= "N is G, A, C, U, dU (i.e.,
            uracil as a substitute base for thymine in
            deoxyribonucleic acid) or T."

( i x ) FEATURE:
        ( A ) NAME/KEY: misc_feature
        ( B ) LOCATION: 11
        ( D ) OTHER INFORMATION: /note= "N is T, A, U, dU (i.e.,
            uracil as a substitute base for thymine in
            deoxyribonucleic acid) or G."

( x i ) SEQUENCE DESCRIPTION: SEQ ID NO:27:

GGNTGGNNGG NTGG                                                                                     14

( 2 ) INFORMATION FOR SEQ ID NO:28:

( i ) SEQUENCE CHARACTERISTICS:

( A ) LENGTH: 15 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: misc_feature
                    ( B ) LOCATION: 3
                    ( D ) OTHER INFORMATION: /note= "N is T, A, U, dU (i.e.,
                            uracil as a substitute base for thymine in
                            deoxyribonucleic acid) or G."

( i x ) FEATURE:
                    ( A ) NAME/KEY: misc_feature
                    ( B ) LOCATION: 7..9
                    ( D ) OTHER INFORMATION: /note= "N is G, A, C, U, dU (i.e.,
                            uracil as a substitute base for thymine in
                            deoxyribonucleic acid) or T."

( i x ) FEATURE:
                    ( A ) NAME/KEY: misc_feature
                    ( B ) LOCATION: 12
                    ( D ) OTHER INFORMATION: /note= "N is T, A, U, dU (i.e.,
                            uracil as a substitute base for thymine in
                            deoxyribonucleic acid) or G."

( x i ) SEQUENCE DESCRIPTION: SEQ ID NO:28:

G G N T G G N N N G   G N T G G                                                                                                 1 5

( 2 ) INFORMATION FOR SEQ ID NO:29:

( i ) SEQUENCE CHARACTERISTICS:
                    ( A ) LENGTH: 16 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: misc_feature
                    ( B ) LOCATION: 3
                    ( D ) OTHER INFORMATION: /note= "N is T, A, U, dU (i.e.,
                            uracil as a substitute base for thymine in
                            deoxyribonucleic acid) or G."

( i x ) FEATURE:
                    ( A ) NAME/KEY: misc_feature
                    ( B ) LOCATION: 7..10
                    ( D ) OTHER INFORMATION: /note= "N is G, A, C, U, dU (i.e.,
                            uracil as a substitute base for thymine in
                            deoxyribonucleic acid) or T."

( i x ) FEATURE:
                    ( A ) NAME/KEY: misc_feature
                    ( B ) LOCATION: 13
                    ( D ) OTHER INFORMATION: /note= "N is T, A, U, dU (i.e.,
                            uracil as a substitute base for thymine in
                            deoxyribonucleic acid) or G."

( x i ) SEQUENCE DESCRIPTION: SEQ ID NO:29:

G G N T G G N N N N   G G N T G G                                                                                               1 6

( 2 ) INFORMATION FOR SEQ ID NO:30:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: misc_feature
                    ( B ) LOCATION: 3
                    ( D ) OTHER INFORMATION: /note= "N is T, A, U, dU (i.e.,
                            uracil as a substitute base for thymine in
                            deoxyribonucleic acid) or G."

( i x ) FEATURE:
    ( A ) NAME/KEY: misc_feature
    ( B ) LOCATION: 7..11
    ( D ) OTHER INFORMATION: /note= "N is G, A, C, U, dU (i.e.,
        uracil as a substitute base for thymine in
        deoxyribonucleic acid) or T."

( i x ) FEATURE:
    ( A ) NAME/KEY: misc_feature
    ( B ) LOCATION: 14
    ( D ) OTHER INFORMATION: /note= "N is T, A, U, dU (i.e.,
        uracil as a substitute base for thymine in
        deoxyribonucleic acid) or G."

( x i ) SEQUENCE DESCRIPTION: SEQ ID NO:30:

GGNTGGNNNN NGGNTGG      17

( 2 ) INFORMATION FOR SEQ ID NO:31:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

GGGTTGGGTC GGTTGGT      17

( 2 ) INFORMATION FOR SEQ ID NO:32:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GGGATGGTTT GGTTGGG      17

( 2 ) INFORMATION FOR SEQ ID NO:33:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

AGGTTGGGAG GGTGGG      16

( 2 ) INFORMATION FOR SEQ ID NO:34:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

TGGTTGGCGA GGATGGA      17

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

AGGTTGGGTA GTGTTGGT 18

( 2 ) INFORMATION FOR SEQ ID NO:36:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:36:

AGGTTGGGCT GGTTGGG 17

( 2 ) INFORMATION FOR SEQ ID NO:37:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:37:

GGGTTGGGAG GTTGGA 16

( 2 ) INFORMATION FOR SEQ ID NO:38:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:38:

TGGTTGGGTC GGTTGGG 17

( 2 ) INFORMATION FOR SEQ ID NO:39:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:39:

GGGATGGTGT GGTTGGC 17

( 2 ) INFORMATION FOR SEQ ID NO:40:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:40:

TGGTTGGCAG GGATGGG 17

( 2 ) INFORMATION FOR SEQ ID NO:41:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:41:

TGGATGGTGA GGTTGGA 17

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:42:

GGGGTGGTTA GGTTGGT           17

(2) INFORMATION FOR SEQ ID NO:43:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:43:

AGGGTGGTTA GGTTGGT           17

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:44:

CGGTTGGGTT GGGATGGA           18

(2) INFORMATION FOR SEQ ID NO:45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:45:

CGGTTGGTGT GGTTGGT           17

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:46:

AGGTTGGTGT GGGTGGG           17

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:47:

CGGGTGGATA GGTTGGA           17

( 2 ) INFORMATION FOR SEQ ID NO:48:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GGTGTGGTAG TTTGTTGGG      19

( 2 ) INFORMATION FOR SEQ ID NO:49:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

TGGTTGGTTA CTGGTTGGG      19

( 2 ) INFORMATION FOR SEQ ID NO:50:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GGGTTGGTCT GGGTGGA      17

( 2 ) INFORMATION FOR SEQ ID NO:51:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

TGGTTGGGTT GGGTGGA      17

( 2 ) INFORMATION FOR SEQ ID NO:52:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

TGGTTGGCCA GGTTGGA      17

( 2 ) INFORMATION FOR SEQ ID NO:53:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CTAGCGGCAG TGGTTGGG      18

( 2 ) INFORMATION FOR SEQ ID NO:54:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:54:

TGGGTGGGGA GGTTGGT 17

( 2 ) INFORMATION FOR SEQ ID NO:55:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:55:

AGGTTGGTTT GGGTGGT 17

( 2 ) INFORMATION FOR SEQ ID NO:56:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:56:

AGGTTGGTTA GGGTTGGT 18

( 2 ) INFORMATION FOR SEQ ID NO:57:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:57:

GGGATGCGGT GGTTGGG 17

( 2 ) INFORMATION FOR SEQ ID NO:58:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:58:

TGGTTGGTTA TGGTTGGT 18

( 2 ) INFORMATION FOR SEQ ID NO:59:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:59:

AGGTTGGTGT GGTTGGC 17

( 2 ) INFORMATION FOR SEQ ID NO:60:

( i ) SEQUENCE CHARACTERISTICS:
  ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:60:

AGGTTGGTGT GGGTGGG                                                                                    17

(2) INFORMATION FOR SEQ ID NO:61:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:61:

TGGTTGGGAG GTTGGT                                                                                     16

(2) INFORMATION FOR SEQ ID NO:62:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:62:

GGGTTGGTGG GTGGATGGT                                                                                  19